(12) United States Patent
Stephens

(10) Patent No.: US 8,728,763 B2
(45) Date of Patent: May 20, 2014

(54) METHODS, PRIMERS, PROBES AND KITS USEFUL FOR THE DETECTION OF BRAF MUTATIONS

(75) Inventor: Craig Stephens, Los Angeles, CA (US)

(73) Assignee: Response Genetics, Los Angeles, CA (US)

(*) Notice: Subject to any disclaimer, the term of this patent is extended or adjusted under 35 U.S.C. 154(b) by 150 days.

(21) Appl. No.: 12/853,746

(22) Filed: Aug. 10, 2010

(65) Prior Publication Data

US 2011/0269124 A1   Nov. 3, 2011

Related U.S. Application Data

(60) Provisional application No. 61/301,790, filed on Feb. 5, 2010, provisional application No. 61/237,078, filed on Aug. 26, 2009, provisional application No. 61/233,054, filed on Aug. 11, 2009.

(51) Int. Cl.
*C12P 19/34*   (2006.01)

(52) U.S. Cl.
USPC ........................................................ 435/91.2

(58) Field of Classification Search
USPC ........................................................ 435/91.2
See application file for complete search history.

(56) References Cited

U.S. PATENT DOCUMENTS

| | | |
|---|---|---|
| 5,256,553 A | 10/1993 | Overell |
| 5,960,210 A | 9/1999 | Jin |
| 5,981,731 A | 11/1999 | Monia |
| 5,994,084 A | 11/1999 | Anderton et al. |
| 6,214,544 B1 | 4/2001 | Fisher |
| 6,391,636 B1 | 5/2002 | Monia |
| 7,189,729 B2 | 3/2007 | Chopiuk et al. |
| 7,202,033 B2 | 4/2007 | Prescott et al. |
| 7,338,957 B2 | 3/2008 | Ding et al. |
| 7,378,233 B2 | 5/2008 | Sidransky et al. |
| 7,442,507 B2 | 10/2008 | Polsky et al. |
| 2005/0186584 A1 | 8/2005 | Stratton et al. |
| 2006/0246476 A1* | 11/2006 | Polsky et al. .................... 435/6 |

FOREIGN PATENT DOCUMENTS

EP   1541695   *   6/2005

OTHER PUBLICATIONS

Lowe et al., Nucleic acids Research, vol. 18, No. 7, pp. 1757-1761, 1990.*

\* cited by examiner

*Primary Examiner* — Cynthia B Wilder
(74) *Attorney, Agent, or Firm* — Hogan Lovells US LLP

(57) ABSTRACT

The present invention relates to methods, primers and probes useful for detecting the presence of mutant BRAF sequences in a sample, specifically for detecting the presence of the BRAF V600E, V600D, V600K, and V600M mutations.

9 Claims, 1 Drawing Sheet

Sequence list of BRAF mutation primers and probes

| SEQ ID NO | SEQUENCE |
|---|---|
| SEQ ID NO: 1 | AAAAATAGGTGATTTTGGTCTAGCTACATA |
| SEQ ID NO: 2 | AATAGGTGATTTTGGTCTAGCTACTGA |
| SEQ ID NO: 3 | AGGTGATTTTGGTCTAGCTACTGC |
| SEQ ID NO: 4 | AATAGGTGATTTTGGTCTAGCTACAAAT |
| SEQ ID NO: 5 | AAAATAGGTGATTTTGGTCTAGCTACTAA |
| SEQ ID NO: 6 | AAAATAGGTGATTTTGGTCTAGCTAGAA |
| SEQ ID NO: 7 | AAATAGGTGATTTTGGTCTAGCTACATAT |
| SEQ ID NO: 8 | AAAATAGGTGATTTTGGTCTAGCTACTAT |
| SEQ ID NO: 9 | AATAGGTGATTTTGGTCTAGCTACACAG |
| SEQ ID NO: 10 | GATCCAGACAACTGTTCAAACTGA |
| SEQ ID NO: 11 | 6FAM-TCCATCGAGATTTC |
| SEQ ID NO: 12 | 6FAM-ACCCACTCCATCGAGA |

METHODS, PRIMERS, PROBES AND KITS USEFUL FOR THE DETECTION OF BRAF MUTATIONS

RELATED APPLICATIONS

This application claims priority to 61/233,054 (filed Aug. 11, 2009); 61/237,078 (filed Aug. 26, 2009) and 61/301,790 (filed Feb. 5, 2010).

FIELD OF THE INVENTION

The present invention relates to methods, primers and probes for detecting the presence of mutant BRAF sequences in a sample, specifically for detecting the presence of the BRAF V600E, V600D, V600K, V600M, and V600A mutations.

BACKGROUND

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor. When a tumor is found, the clinical objective is to destroy malignant cells selectively while mitigating any harm caused to normal cells in the individual undergoing treatment.

B-raf (or BRAF) encodes a protein that belongs to the Serine/Threonine protein kinases. BRAF is a part of the Ras/Raf/MEK/MAP signal transduction pathway and plays a role in regulating the MAP Kinse/ERK signaling pathway. Mutations in this gene have been associated with various cancers such as colorectal cancer (CRC), non small cell lung cancer (NSCLC), malignant melanomas and adenocarcinomas. Oncogenic mutations in BRAF, nearly all of which are the V600E mutation, have been reported in colon cancer (Davies H, et al. Nature 2002; 417:949-54; Rajagopalan H, et al., Nature 2002; 418:934.). The V600E mutation has been observed in over half of all microsatellite-unstable carcinomas and in a much smaller subset of stable colon tumors (Wang L, et al., Cancer Res 2003; 63:5209-12). The V600E (formerly V599E) mutation is located on exon 15 of the B-raf gene (Accession number NM_04333.4) at position 1860 (1799 of the coding sequence). At position 1799 of the coding sequence, a thymidine is changed to an adenosine, which results in the change from a valine (V) in the wildtype/non mutant B-rag gene to a Glutamine (E) in the mutated gene. In addition, a rare (<1%) V600K (1798-1799 GT>AA) mutation also exists. Furthermore, the V600D mutation exists in 4.6% of cases, the V600A mutation exists in <1% of cases, and the V600M mutation exists in <1% of cases. In addition, there are V600R and K601E BRAF mutations.

The V600E BRAF mutation is found in a number of tissue/tumor types including: nervous system, thyroid, skin, gastrointestinal tract, large intestine, biliary tract, ovary, eye, prostate, central nervous system, liver, small intestine, breast, pancreas, soft tissue, upper, aerodigestive tract, adrenal gland, autonomic ganglia, haematopoietic and lymphoid tissue, lung, esophagus, pituitary, and stomach. DNA or RNA extracted from samples of any of these types of tissues can be utilized in assays of the present invention.

In both stable and unstable cancers, >90% of tumors with BRAF mutations have widespread methylation of CpG islands or what is known as the CpG island methylator phenotype (CIMP). Improved survival associated with microsatellite instability (MSI) in sporadic colon cancers has been reported (Samowitz WS, et al., Cancer Epidemiol Biomarkers Prey 2001; 10:917-23; Halling KC, et al., J Natl Cancer Inst 1999; 91:1295-303), and because sporadic unstable tumors commonly show both CIMP (Toyota M, et al., Proc Natl Acad Sci USA 1999; 96:8681-6; Toyota M, et al., Proc Natl Acad Sci USA 2000; 97:710-5) and BRAF mutations (Kambara T, et al., Gut 2004; 53:1137-44; Nagasaka T, et al., J Clin Oncol 2004; 22:4584-94), one would expect that these features would also show a relationship to improved survival in unstable tumors. Samowitz has studied the relationship between CIMP and survival in microsatellite-stable tumors and has evaluated the relationship between BRAF mutations and survival in microsatellite-stable colon cancers. See Samowitz, Wade S., et al., Cancer Research 65, 6063-6069, Jul. 15, 2005. Samowitz has evaluated a large population-based sample of individuals with colon cancer to determine its relationship to survival and other clinicopathologic variables. The V600E BRAF mutation was seen in 5% of microsatellite-stable tumors and 51.8% of microsatellite-unstable tumors. In microsatellite-stable tumors, this mutation was related to poor survival, CIMP high, advanced American Joint Committee on Cancer (AJCC) stage, and family history of colorectal cancer. The poor survival was observed in a univariate analysis of 5-year survival (16.7% versus 60.0%); in an analysis adjusted for age, stage, and tumor site; in stage-specific, age-adjusted analyses for AJCC stages 2 to 4 (HRR, 4.88, 3.60, and 2.04, respectively); and in Kaplan-Meier survival estimates for AJCC stages 2 to 4. Microsatellite-unstable tumors were associated with an excellent 5-year survival whether the V600E mutation was present or absent (76.2% and 75.0%, respectively). Samowitz has concluded that the BRAF V600E mutation in microsatellite-stable colon cancer is associated with a significantly poorer survival in stages 2 to 4 colon cancer but has no effect on the excellent prognosis of microsatellite-unstable tumors.

Moreover, BRAF mutations proved to be absent in tumors from hereditary nonpolyposis colorectal cancer syndrome (HNPCC) families with germline mutations in the MMR genes MLH1 and MSH2. These data suggest that the oncogenic activation of BRAF is involved only in sporadic colorectal tumorigenesis. The detection of a positive BRAF-V600E mutation in a colorectal cancer suggests a sporadic origin of the disease and the absence of germline alterations of MLH1, MSH2 and also of MSH6. These findings have a potential impact in the genetic testing for HNPCC diagnostics and suggest a potential use of BRAF as exclusion criteria for HNPCC or as a molecular marker of sporadic cancer. See Domingo et al., Oncogene (2005) 24, 3995-3998.

Solit's group have found, using small-molecule inhibitors of MEK and an integrated genetic and pharmacologic analysis, that mutation of BRAF is associated with enhanced and selective sensitivity to MEK inhibition when compared to either 'wild-type' cells or cells harboring a RAS mutation. This MEK dependency was observed in BRAF mutant cells regardless of tissue lineage, and correlated with both down regulation of cyclin D1 protein expression and the induction of G1 arrest. Pharmacological MEK inhibition completely abrogated tumor growth in BRAF mutant xenografts, whereas RAS mutant tumors were only partially inhibited. These data suggest an exquisite dependency on MEK activity in BRAF mutant tumors, and offer a rational therapeutic strategy for this genetically defined tumor subtype. See Solit, David B., et al., Nature 439, 358-362 (19 Jan. 2006).

In addition, a model of human melanocyte transformation has emerged based on the results of genetic studies, cell biology, molecular pathology and mouse modeling. Studies have identified involvement of various factors including basic fibroblast growth factor production, ERK activation, and frequent BRAF mutations in melanoma tissues. BRAF acts downstream of RAS, and studies have demonstrated that simultaneous mutations in RAS and BRAF are extremely rare in melanoma, suggesting that BRAF mutations substitute for at least some of the oncogenic function of mutant RAS.

The development of tumor markers to better stratify patients for their risk of developing metastases is under active investigation. Although assessment of tumor markers and selection of treatment based on the results has been part of the standard of care in colon and breast cancer management for several years, no such markers exist for melanoma. Many studies have shown promise, but none have moved past the preliminary stages of development into a clinically useful assay.

Despite recent advances in the study of melanoma biology, the development of molecular tools useful for diagnosing and/or monitoring patients with melanoma is still relatively new. Few advances have been made in protocols designed to monitor patients for disease recurrence, or to select patients at high risk for the development of metastases. Tumor stage, the best predictor of survival from melanoma, is based on conventional clinicopathologic variables such as thickness and ulceration of the primary tumor, and the presence of metastatic disease in regional lymph nodes or at distant sites. Two patients with primary tumors of intermediate thickness that appear microscopically identical can, however, have dramatically different survivals. The absence of improved prognostic tools for such assessments makes it difficult for attending physicians to determine the best treatment strategies.

Mutations in the BRAF oncogene have been discovered in up to 80% of melanoma tissues, frequencies strikingly higher than any other molecular alteration in this disease. BRAF mutations have also been detected in tumor tissues from other types of cancer. Experimental studies have demonstrated that several BRAF mutations, especially the T1799A (formerly designated T1796A) hotspot mutation, which accounts for 90% of BRAF mutations in melanoma, can transform fibroblasts in culture. Most recently, experiments blocking the expression of mutant BRAF in melanoma cell culture were shown to inhibit cell growth and promote cell death, suggesting that BRAF inhibitors could bolster melanoma treatment significantly.

SUMMARY OF THE INVENTION

The present invention discloses methods of detecting BRAF V600E, V600D, V600K, V600M, and V600A mutations in a sample. The present invention discloses compositions comprising primer and probe sequences used in the amplification and detection of V600E, V600D, V600K, V600M, or V600A mutant BRAF sequences present in samples. Particular primer combinations as disclosed herein are used in amplifying particular BRAF mutations. It will be appreciated by those skilled in the art, one may also design primers specific to the 1798-1799 GT>AA double mutation.

BRIEF DESCRIPTION OF THE DRAWINGS

FIG. 1 shows the primers and probes used in the amplification and detection of BRAF mutations.

DETAILED DESCRIPTION OF THE INVENTION

The present invention provides methods, primers, probes and kits useful for the detection of BRAF mutations. The methods, primers, probes and kits of the present invention can be used for detecting the BRAF V600E, V600D, V600K, V600M, and V600A mutations in many different cell types and thus can be used for the diagnosis of many different cancers, such as, but not limited to, melanoma, colorectal cancer, lung cancer and thyroid cancer. The methods of the invention may be useful as a predictor of outcome for cancer patients. One of the key factors that contribute to improved outcome for a patient with any disease and in particular cancer, due to its progressive and invasive nature, is early and accurate diagnosis. The method of the present invention addresses the desperate need for a rapid, non-invasive, and accurate screening assay for detecting mutant BRAF sequences, the presence of which is a positive indicator of metastasizing disease. As such, it identifies those patients who need to be treated with more aggressive treatment regimens. Moreover, since the invention can be used for either DNA or RNA, sample preparation is facile, thereby reducing assay variability that can result from differences in the expertise level of laboratory technicians involved in sample preparation.

As a non limiting example, the method of the present invention may be used to monitor patients with advanced, metastatic melanoma (Stages III/IV). These patients are at the highest risk for disease progression, and early detection of an increase in disease activity would lead to earlier treatment and improvement in outcome. The method of the present invention may also be directed to testing patients with earlier stages of disease (Stages I/II), who are at risk for metastatic spread of their disease. Again, early intervention with additional diagnostic tests and treatments would lead to improved patient survival.

The present invention provides a method for detecting the presence of a BRAF mutation in a sample, said method comprising: (a) isolating nucleic acid from said sample wherein the sample comprises nucleic acid sequences; (b) performing an amplification reaction of said nucleic acid sequences of said sample, wherein said amplification reaction comprises a first primer capable of annealing specifically to a BRAF mutant sequence at a first position in a BRAF sequence wherein said first primer is SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 and a second primer capable of annealing specifically at a second position in a BRAF sequence wherein said second primer is SEQ ID NO: 10, wherein said first and second primers anneal to different strands of double stranded BRAF sequence, wherein the amplification reaction is capable of producing a BRAF mutant specific amplification product when the sequences of the sample comprise a BRAF sequence comprising a mutant sequence at said first position of said BRAF sequence; and (c) visualizing amplification products produced by said amplification reaction, wherein detection of a BRAF mutant specific amplification product is a positive indicator of the presence of a BRAF mutation in said sample.

The present invention also provides a method for detecting the presence of metastatic melanoma in a sample, said method comprising: (a) isolating nucleic acid from said sample wherein the sample comprises nucleic acid sequences; (b) performing an amplification reaction of said nucleic acid sequences of said sample, wherein said amplification reaction comprises a first primer capable of annealing specifically to a BRAF mutant sequence at a first position in a BRAF sequence wherein said first primer is SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 and a second primer capable of annealing specifically at a second position in a BRAF sequence wherein said second primer is SEQ ID NO: 10, wherein said first and second primers anneal to different strands of double stranded BRAF sequence, wherein the amplification reaction is capable of producing a BRAF mutant specific amplification product when the sequences of the sample comprise a BRAF sequence comprising a mutant sequence at said first position of said BRAF sequence; and (c) visualizing amplification products produced by said amplification reaction, wherein detection of a BRAF mutant specific amplification product is a positive indicator of metastatic melanoma in said sample.

Embodiments of the present invention comprise BRAF V600E, V600D, V600K, V600M, and V600A mutant specific primers. Exemplary BRAF V600 E mutant specific primer pairs include SEQ ID NO: 1, SEQ ID NO: 2, or SEQ ID NO: 9 and SEQ ID NO: 10. Exemplary BRAF V600D mutant specific primer pairs include SEQ ID NO: 1, SEQ ID NO: 2, SEQ ID NO: 4, or SEQ ID NO: 7 and SEQ ID NO: 10. Exemplary BRAF V600K mutant specific primer pairs include SEQ ID NO: 1, SEQ ID NO: 4, SEQ ID NO: 5, or SEQ ID NO: 6 and SEQ ID NO: 10. Exemplary BRAF V600M mutant specific primer pairs include SEQ ID NO: 6 or SEQ ID NO: 8 and SEQ ID NO: 10. Exemplary BRAF V600A specific primers include SEQ ID NO: 3 and SEQ ID NO: 10. These primers were designed to avoid any known BRAF polymorphisms. As described herein, such oligonucleotides can be detectably labeled.

BRAF V600 mutant specific primers (SEQ ID NO:1; SEQ ID NO:2; SEQ ID NO:3, SEQ ID NO: 4, SEQ ID NO: 5, SEQ ID NO: 6, SEQ ID NO: 7, SEQ ID NO: 8, SEQ ID NO: 9, SEQ ID NO: 10) or appropriate BRAF mutant specific primer pairs may be components of compositions comprising biologically compatible salt solutions and/or other buffers or components.

Embodiments of the present invention comprise oligonucleotide probe sequences, SEQ ID NO: 11 and SEQ ID NO: 12, wherein the oligonucleotide is used as a probe for the detection of BRAF mutant sequences. This probe was designed to avoid any known BRAF polymorphisms. Optionally, the oligonucleotide is detectably labeled.

The present invention also provides a kit comprising at least one of SEQ ID NO: 1-12.

Embodiments of the present invention can be utilized to detect the V600E, V600D, V600K, V600M, and V600A BRAF mutations.

Samples

The method comprises obtaining a sample of a tissue or a body fluid from the subject (e.g., a mammal) wherein the sample contains nucleic acid. Non-limiting examples of tissue or body fluids that can be used include blood, plasma, lymph, tumor biopsies, and body tissue. In one embodiment, the tissue sample comprises paraffin embedded tissue specimens. In some embodiments, the nucleic acid is deoxyribonucleic acid (DNA). In some embodiments, the nucleic acid is ribonucleic acid (RNA).

The present method can be applied to any type of tissue from a patient. Sources of such tissue include but are not limited to nervous system, thyroid, skin, gastrointestinal tract, large intestine, biliary tract, ovary, eye, prostate, central nervous system, liver, small intestine, breast, pancreas, soft tissue, upper, aerodigestive tract, adrenal gland, autonomic ganglia, haematopoietic and lymphoid tissue, lung, esophagus, pituitary, and stomach. For examination of resistance of tumor tissue, it is preferable to examine the tumor tissue. In a preferred embodiment, a portion of normal tissue from the patient from which the tumor is obtained is also examined.

The methods of the present invention can be applied over a wide range of tumor types. This allows for the preparation of individual "tumor expression profiles" whereby expression levels of BRAF V600E, V600D, V600K, V600M, or V600A mutant sequences are determined in individual patient samples and response to various chemotherapeutics is predicted. In certain embodiments, the methods of the invention are applied to colon cancer or melanoma tumors.

Isolating Nucleic Acid

Embodiments of the present invention utilize methods of DNA isolation known to those skilled in the art. In general, the aim is to separate DNA present in the nucleus of the cell from other cellular components. The isolation of DNA usually begins with lysis, or breakdown, of tissue or cells. This process is essential for the destruction of protein structures and allows for release of nucleic acids from the nucleus. Lysis is carried out in a salt solution, containing detergents to denature proteins or proteases (enzymes digesting proteins), such as Proteinase K, or in some cases both. It results in the breakdown of cells and dissolving of membranes. Methods of DNA isolation include, but are not limited to, phenol:chloroform extraction, high salt precipitation, alkaline denaturation, ion exchange column chromatography, resin binding, and paramagnetic bead binding.

Embodiments of the present invention utilize methods of RNA isolation known to those skilled in the art. RNA may be isolated and prepared for hybridization by a variety of methods including, but not limited to, Trizol® and Guanidinium thiocyanate-phenol-chloroform extraction. The principle of RNA isolation is based on cell/tissue lysis, followed by extraction, precipitation, and washing. It will be understood by those skilled in the art the selection of RNA isolation will depend on sample type. Incorporated by reference is U.S. Ser. No. 12/144,388 directed to a method of RNA isolation from paraffin embedded tissue, a common source for oncogene marker testing.

Amplification

Embodiments of the present invention utilize thermal and isothermal amplification methods including, but not limited to, polymerase chain reaction (PCR), reverse transcriptase polymerase chain reaction (RT-PCR), ligase chain reaction (LCR), helicase dependent amplification (HDA) and Nucleic Acid Sequence Based Amplification (NASBA) and Amplification Refractory Mutation System (ARMS). In a preferred embodiment, the primers and probes are used in ARMS.

Detection

Embodiments of the present invention utilize detection methods including, but not limited to, labeling primers used during the amplification step such that the amplification products are labeled with a detectable marker and hybridizing the amplification product to oligonucleotide probes labeled with a detectable marker. Detectable markers include but are not limited to chemiluminescent tags, fluorescent tags, and radioactive tags. Labeled amplification product can be directly measured using methods corresponding to the type of label used according to methods would be known to one skilled in the art. Labeled probe can be hybridized to the amplification product according to methods known to one skilled in the art.

In performing the method of the present invention BRAF V600E mutant expression levels are assayed in patient tumor samples to prognosticate the efficacy a treatment regimen. In performing the method of the present invention BRAF V600E mutant expression levels are assayed in patient tumor samples to predict the efficacy a treatment regimen. In performing the method of the present invention BRAF V600D mutant expression levels are assayed in patient tumor samples to predict the efficacy a treatment regimen. In performing the method of the present invention BRAF V600K mutant expression levels are assayed in patient tumor samples to predict the efficacy a treatment regimen. In performing the method of the present invention BRAF V600M mutant expression levels are assayed in patient tumor samples to predict the efficacy a treatment regimen. In performing the method of the present invention BRAF V600A mutant expression levels are assayed in patient tumor samples to predict the efficacy a treatment regimen.

In performing the method of this embodiment of the present invention, tumor cells are preferably isolated from the patient. Solid or lymphoid tumors or portions thereof are surgically resected from the patient or obtained by routine biopsy. RNA isolated from frozen or fresh samples is extracted from the cells by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of the RNA during the extraction process.

Example 2

Detection of V600K BRAF Mutation

The rare V600K BRAF mutation can be detected utilizing the same pair of primers designed for the V600E mutation. The V600K mutation is a 1798-1799 GT>AA double mutation. SEQ ID NO:2 comprises a highly specific primer that will only result in amplified product in the presence of the single 1799 T>A mutation. Thus, when performing amplification reactions utilizing primer pairs SEQ ID NO:1 and SEQ ID NO: 10, and another reaction on the same sample utilizing primer pairs SEQ ID NO:2 and SEQ ID NO: 10, the first reaction will provide amplified product (positive) whereas the second reaction will not provide product (negative). This combination of positive and negative results indicates the presence of the V600K mutation.

TABLE 1

| Primer Name | Sequence | Predicted Mutation Detection |
|---|---|---|
| Braf_1799A_1GT-F | AAAAATAGGTGATTTTGGTCTAGCTACAT<u>A</u> | 600E, 600D and 600K |
| Braf_1799A_2AT-F | AATAGGTGATTTTGGTCTAGCTACTG<u>A</u> | 600E and 600D |
| Braf_V600A_2AT-F | AGGTGATTTTGGTCTAGCTACTG<u>C</u> | 600A Only |
| Braf_V600D_2GA-F | AATAGGTGATTTTGGTCTAGCTACAA<u>AT</u> | 600D and 600K (weak) |
| Braf_V600K_2AT-F | AAAATAGGTGATTTTGGTCTAGCTACT<u>AA</u> | 600K Only |
| Braf_V600M_2CG-F | AAAATAGGTGATTTTGGTCTAGCTA<u>A</u>A | 600K and 600M |
| Braf_V600D_2GC-F3 | AAATAGGTGATTTTGGTCTAGCTACAT<u>AT</u> | 600D Only |
| Braf_V600M_2GT-F2 | AAAATAGGTGATTTTGGTCTAGCTACT<u>A</u>T | 600M Only |
| Braf_1799A_2GC-F | AATAGGTGATTTTGGTCTAGCTACACAG | V600E |
| Common Reverse Primer (used with ALL above Forward primers) | | |
| 2Braf_C600-R | GATCCAGACAACTGTTCAAACTGA | |
| Common Probe (used with ALL primer combinations) | | |
| Braf_C600-Mc2 | 6FAM-TCCATCGAGATTTC | |
| Braf_C600-Mc3 | 6FAM-ACCCACTCCATCGAGA | |

X base = secondary mutation
XX base = mutation of interest

EXAMPLES

Example 1

Testing of the Primers of the Present Invention

A synthetic V600E construct was made to test the ability of the primers and the probes of the present invention to specifically amplify a nucleic acid containing a BRAF V600E mutation. Two set of Primers/probes for BRAF V600E mutation were used for the validation. The V600E synthetic construct was serially diluted (1:2) 17 times in a background of gDNA (0.67 ng/uL, 5 ng/PCR). The mutation concentration ranged from 10 fM to 0.15 aM. Each diluted sample was assayed 6× in duplicate (12 total) for the control (Exon13) and the V600E mutation.

Example 3

BRAF T1799A/GT1798-1799AA/TG1799-1800AT Mutation Exclusivity Test

A) Test Material
1. DNA synthetic fragments were generated that contained the BRAF V600 D, E, and K mutations a. BRAF V600D:
AGTAAAAATAGGTGATTTTGGTCTAGCTACAGATAAATCTCGAT
GGAGTGGGTCCCATCAGTTTGAACAGTTGTCTGGATCCATTT b. BRAF V600E c. BRAF V600K:
ACAGTAAAAATAGGTGATTTTGGTCTAGCTACAAAGAAATCTC
GATGGAGTGGGTCCCATCAGTTTGAACAGTTGTCTGGATCCATT
TT 2. Sequence specific primers/probes for BRAF mutations V600 D, E and K mutations (sequence listed in Table 1)
   a. 1799A__1GT (specific for 1799 T to A base pair change (V600E, V600D and V600K)
   b. V600D__2GA (specific for V600D)
   c. V600K__2AT (specific for V600K)

B. Procedure
   1. Dilute each of three synthetic fragments to a concentration of 200 aM in 0.667 ng/ul of Genomic DNA (Promega Corp.—human genomic DNA, 100 ug)
   2. PCR amplify the synthetic specific fragments for each mutation with all three primer sets (specific for each mutation
   3. Analyze exclusivity C. Analysis of Exclusivity
   The following two primer/probe sets have been designed to amplify specific mutations. These primers were tested with each of the synthetic fragments to test for exclusivity
      a. 1799A__1GT (Amplifies V600E, V600D and V600K) This primer/probe set has been described in the assay development section (7) to amplify a T to A change at base 1799.
      b. V600D__2GA (specific for V600D) This primer/probe set has been described in the assay development section (7) to amplify a TG change to AT at base 1799-1800.
      c. V600K__2AT (specific for V600K) This primer/probe set has been described in the assay development section (7) to amplify a CT change to AA at base 1798-1799.
   All primers and probes were used in the exclusivity testing
   Results: The following table describes fragments that were successfully amplified with specific primer probe sets. A plus (+) signifies that a specific fragment was amplified.

TABLE 2

The combination of primers to define each mutant type are the following

| 1799A__1GT | V600K__2AT | V600D__2GA | Mutant |
|---|---|---|---|
| + | − | − | V600E |
| + | − | + | V600D |
| + | + | − | V600K |
| − | − | − | wild type |
| − | − | − | invalid |

Results:
We collected Ct data for each synthetic and primer/probe combination

| | V600D Synthetic Ct | V600E Synthetic Ct | V600K Synthetic Ct |
|---|---|---|---|
| V600D__2GA (amplifies only V600D) | 30.39 | 36.87 | 33.79 |

-continued

| | V600D Synthetic Ct | V600E Synthetic Ct | V600K Synthetic Ct |
|---|---|---|---|
| 1799A__1GT (amplifies V600D, V600E, and V600K) | 30.34 | 30.65 | 29.61 |
| V600K__2AT (amplifies only V600K) | 39.06 | 38.72 | 29.67 |

Exclusivity was determined by subtracting Cts of the PCR amplification of each template using primer/probe sets designed to be specific and non-specific for each template

| | V600D Synthetic Delta Ct | V600E Synthetic Delta Ct | V600K Synthetic Delta Ct |
|---|---|---|---|
| V600D__2GA (amplifies only V600D) | 0 | 6.22 | 4.12 |
| 1799A__1GT (amplifies V600D, V600E, and V600K) | −0.05 | 0 | −0.06 |
| V600K__2AT (amplifies only V600K) | 8.67 | 8.07 | 0 |

The delta Cts were determined as follows:
Example:
Exclusivity of the V600D__2GA for V600D synthetic fragment=0
Using V600 D fragment as the template amplification was performed with V600D__2GA primer/probes
$dCt=30.39-30.39=0$ (exclusive)

Using V600 D fragment as the template amplification was performed with 1799A__1GT primer/probes
$dCT=30.34-30.39=-0.05$ (exclusive)

Using V600 D fragment as the template amplification was performed with V600K__2AT primer/probes
$dCT=39.06-30.39=8.67$ (non-specific)

Acceptance Criteria
   $dCT$(Ct using primers specific for the fragment−Ct using primers non-specific for the fragment)≤4

Preset Acceptance criteria described in section 7 (assay development—see following table) that primer/probe 1799__1GT would detect a T to A base pair change at 1799 and, therefore, would detect all mutations.
Results:
V600K__2AT is exclusive for V600K mutation
V600D__2GA is exclusive for V600D mutation
1799A__1GT is exclusive for 1799 T to A change which is contained in all three mutations (V600E, V600E and V600K)

TABLE 3

The combination of primers to define each mutant type

| BrafEx13 | 1799A__1GT | 1799A__2AT | V600K__2AT | V600D__2GA | Mutant |
|---|---|---|---|---|---|
| + | + | + | − | − | V600E |
| + | + | − | − | + | V600D |
| + | + | − | + | − | V600K |

TABLE 3-continued

The combination of primers to define each mutant type

| BrafEx13 | 1799A_1GT | 1799A_2AT | V600K_2AT | V600D_2GA | Mutant |
|---|---|---|---|---|---|
| + | – | – | – | – | wild type |
| >30 Ct | – | – | – | – | invalid |

The invention claimed is:

1. A method for detecting the presence of a BRAF mutation in a sample, said method comprising:
   (a) isolating a nucleic acid from said sample, wherein the sample is a FFP formalin-fixed paraffin-embedded (FFPE) tissue sample, wherein the sample comprises DNA sequences;
   (b) performing an amplification reaction of said DNA sequences of said sample, wherein said amplification reaction comprises a first primer capable of annealing specifically to a BRAF mutant sequence at a first position in a BRAF DNA sequence wherein said first primer consists of SEQ ID NO:1, SEQ ID NO:2, SEQ ID NO: 3, SEQ ID NO: 4, SEQ ID NO: 5, SEQ ID NO: 6, SEQ ID NO: 7, SEQ ID NO: 8, or SEQ ID NO: 9 and a second primer capable of annealing specifically at a second position in a BRAF DNA sequence, wherein said first and second primers anneal to different strands of double stranded BRAF DNA sequence, wherein the amplification reaction is capable of producing a BRAF mutant specific amplification product when the DNA sequences of the sample comprise a BRAF DNA sequence comprising a mutant sequence at said first position of said BRAF DNA sequence; and
   (c) visualizing amplification products produced by said amplification reaction, wherein detection of a BRAF mutant specific amplification product is a positive indicator of a BRAF mutation in said sample.

2. A method for detecting the presence of a BRAF mutation in a sample, said method comprising:
   (a) isolating a nucleic acid from said sample wherein the sample comprises RNA sequences wherein the sample is a FFP formalin-fixed paraffin-embedded (FFPE) tissue sample;
   (b) performing an amplification reaction of said RNA sequences of said sample, wherein said amplification reaction comprises a first primer capable of annealing specifically to a BRAF mutant sequence at a first position in a BRAF RNA sequence wherein said first primer consists of SEQ ID NO:1, SEQ ID NO:2, SEQ ID NO: 3, SEQ ID NO: 4, SEQ ID NO: 5, SEQ ID NO: 6, SEQ ID NO: 7, SEQ ID NO: 8, or SEQ ID NO: 9 and a second primer capable of annealing specifically at a second position in a BRAF RNA sequence, wherein said first and second primers anneal to different strands of double stranded BRAF RNA sequence, wherein the amplification reaction is capable of producing a BRAF mutant specific amplification product when the RNA sequences of the sample comprise a BRAF RNA sequence comprising a mutant sequence at said first position of said BRAF RNA sequence; and
   (c) visualizing amplification products produced by said amplification reaction, wherein detection of a BRAF mutant specific amplification product is a positive indicator of a BRAF mutation in said sample.

3. The method of claim 1 wherein the presence of the BRAF mutation is a positive indicator of metastatic melanoma in said sample.

4. The method of claim 2 wherein the presence of the BRAF mutation is a positive indicator of metastatic melanoma in said sample.

5. The method of claim 1 wherein the BRAF mutation is selected from the group consisting of BRAF V600E, BRAF V600D, BRAF V600K, BRAF V600M, and BRAF V600A mutations.

6. The method of claim 1, wherein the sample is selected from the group consisting of blood, tissue, or cells.

7. The method of claim 1, wherein the tissue sample is formalin fixed paraffin embedded tissue.

8. The method of claim 1, wherein said second primer capable of annealing specifically at a second position in a BRAF nucleic acid sequence consists of SEQ ID NO: 10.

9. The method of claim 2 wherein the BRAF mutation is selected from the group consisting of BRAF V600E, BRAF V600D, BRAF V600K, BRAF V600M, and BRAF V600A mutations.

* * * * *

SEQUENCE LISTING

<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaaataggt gattttggtc tagctacata                                    30

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aataggtgat tttggtctag ctactga                                       27

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggtgatttt ggtctagcta ctgc                                          24

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aataggtgat tttggtctag ctacaaat                                      28

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaataggtg attttggtct agctactaa                                     29

```
<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaaataggtg attttggtct agctagaa                                       28

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaataggtga ttttggtcta gctacatat                                      29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaaataggtg attttggtct agctactat                                      29

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aataggtgat tttggtctag ctacacag                                       28

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatccagaca actgttcaaa ctga                                           24

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tccatcgaga tttc                                                      14
```

```
<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
acccactcca tcgaga                                                      16

<210> SEQ ID NO 13
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agtaaaaata ggtgattttg gtctagctac agataaatct cgatggagtg ggtcccatca     60
gtttgaacag ttgtctggat ccattt                                          86

<210> SEQ ID NO 14
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acagtaaaaa taggtgattt tggtctagct acaaagaaat ctcgatggag tgggtcccat     60
cagtttgaac agttgtctgg atccatttt                                       89
```